US009764099B2

(12) United States Patent
Rimsa et al.

(10) Patent No.: US 9,764,099 B2
(45) Date of Patent: Sep. 19, 2017

(54) SYRINGE WITH TEMPERATURE MODULATION CAPABILITIES

(75) Inventors: Joseph Rimsa, Menlo Park, CA (US); Kenneth Horne, San Francisco, CA (US)

(73) Assignee: TauTona Group LP, Menlo Park, CA (US)

( * ) Notice: Subject to any disclaimer, the term of this patent is extended or adjusted under 35 U.S.C. 154(b) by 320 days.

(21) Appl. No.: 14/357,761

(22) PCT Filed: Sep. 13, 2012

(86) PCT No.: PCT/US2012/055145
§ 371 (c)(1),
(2), (4) Date: Jul. 30, 2015

(87) PCT Pub. No.: WO2013/040197
PCT Pub. Date: Mar. 21, 2013

(65) Prior Publication Data
US 2015/0352292 A1    Dec. 10, 2015

Related U.S. Application Data

(60) Provisional application No. 61/534,293, filed on Sep. 13, 2011.

(51) Int. Cl.
*A61M 5/44* (2006.01)
*A61M 5/31* (2006.01)
*A61M 5/178* (2006.01)
*A61B 17/00* (2006.01)
(Continued)

(52) U.S. Cl.
CPC .............. *A61M 5/44* (2013.01); *A61M 5/178* (2013.01); *A61M 5/3129* (2013.01); *A61M 5/3137* (2013.01); *A61B 2017/00734* (2013.01); *A61M 5/145* (2013.01); *A61M 5/445* (2013.01); *A61M 25/0043* (2013.01); *A61M 2205/3606* (2013.01); *A61M 2205/3653* (2013.01); *A61M 2205/8206* (2013.01)

(58) Field of Classification Search
CPC ................................ A61M 5/44; A61M 5/445
See application file for complete search history.

(56) References Cited

U.S. PATENT DOCUMENTS 1,677,642 A * 7/1928 Kirk .................... A61M 3/0279
604/114
2,420,338 A * 5/1947 Page .................... A61C 1/0007
392/468
(Continued)

OTHER PUBLICATIONS

International Search Report for PCT/US2012/055145 dated Mar. 21, 2013 (7 pages).

*Primary Examiner* — Nathan R Price
*Assistant Examiner* — John Doubrava
(74) *Attorney, Agent, or Firm* — Sheppard Mullin Richter & Hampton LLP (57) ABSTRACT

Disclosed herein are syringes having temperature modulation capabilities particularly with regard to changing the temperature of the material being ejected from or injected into the syringe and methods of use. In a specific embodiment of this invention, the syringe comprises a phase transition composition which is to be maintained in one phase within the syringe chamber and ejected in a different phase from the syringe.

6 Claims, 4 Drawing Sheets

(51) Int. Cl.
 *A61M 5/145* (2006.01)
 *A61M 25/00* (2006.01)

(56) References Cited

U.S. PATENT DOCUMENTS

| | | | | |
|---|---|---|---|---|
| 4,582,488 A | * | 4/1986 | Newman | A61C 5/045 433/81 |
| 6,036,955 A | * | 3/2000 | Thorpe | A61K 47/48561 424/130.1 |
| 6,139,571 A | * | 10/2000 | Fuller | A61F 7/12 604/113 |
| 6,440,103 B1 | * | 8/2002 | Hood | A61F 9/00736 604/113 |
| 6,511,660 B1 | * | 1/2003 | Lin | A61K 9/0048 424/78.04 |
| 2006/0222350 A1 | * | 10/2006 | Cassidy | A61M 5/44 392/470 |
| 2006/0271014 A1 | | 11/2006 | Hynes et al. | |
| 2007/0293820 A1 | | 12/2007 | Dacquay et al. | |
| 2008/0045985 A1 | * | 2/2008 | Gurtner | A61B 17/00491 606/154 |
| 2009/0177182 A1 | * | 7/2009 | Hickingbotham | A61F 9/0017 604/506 |
| 2010/0204718 A1 | | 8/2010 | Rappleye et al. | |
| 2010/0286654 A1 | * | 11/2010 | Dos Santos | A61M 5/44 604/506 |
| 2011/0137318 A1 | | 6/2011 | Liao et al. | |

\* cited by examiner

SYRINGE WITH TEMPERATURE MODULATION CAPABILITIES

CROSS REFERENCE TO RELATED APPLICATIONS

This application is a National Phase application under 35 U.S.C. §371 of PCT Application PCT/US2012/055145, filed Sep. 13, 2012, which claims the benefit under 35 U.S.C. §119(e) to U.S. Provisional Application No. 61/534,293, filed on Sep. 13, 2011, the contents of which are hereby incorporated by reference in their entirety.

BACKGROUND

Field

This disclosure is directed to syringes having temperature modulation capabilities, particularly with regard to changing the temperature of the material being ejected from or injected into the syringe. In a specific embodiment of this invention, the syringe comprises a phase transition composition which is to be maintained in one phase within the syringe chamber and ejected in a different phase from the syringe.

State of the Art

Many compositions require a temperature change before injection into in a subject. In one case, pharmaceutical formulations suitable for, e.g., intraveneuos injection, are often unstable at room or body temperatures and must be refrigerated to ensure proper efficacy for the administered drug. However, as is apparent, these compositions are typically allowed to reach at least room temperature prior to administration and the time required to achieve room temperature delays administration.

Likewise, phase transition compositions have been disclosed for use in treating patients. In one embodiment, phase transition compositions can be used to fill a lumen in the patient. Such lumens include blood vessels as during surgical procedures, vas deferens to effect male sterilization, fallopian tubes to effect female sterilization, intestinal tracts, and the like. The phase transition composition can be introduced in its liquid phase and then allowed to phase transition to its solid phase when exposed long enough to body temperature. See, for example, United States Patent Application Publication No. 2007/0191768 and U.S. Pat. No. 7,160,931.

One particular embodiment that has drawn significant interest is the use of phase transition compositions during surgical procedures such as anastomosis. See, for example, United States Patent Application Publication Nos. 2008/0045985 and 2008/0031847.

One limitation with using phase transition compositions is that their transition from a solid to a liquid phase or from a liquid to a solid phase occurs over a temperature range. The broader the temperature range, the more likely that the composition will stay in the "undesired" phase before converting to the "desired" phase. This delay may result in difficulty for the surgeon to assess whether the phase transition has been completed prior to initiating the surgical procedure. When a poloxamer is used in the phase transition composition, one attempt to minimize this delay has been to purify the poloxamer to a narrow molecular weight range such that the phase transition temperature will occur over a narrower temperature range. See, for example, United States Patent Application Publication No. 2008/0031847.

Notwithstanding the benefits alleged by the approach, the surgeon is still left with the task of evaluating when the composition has completed its phase transition. If a surgical procedure is initiated before phase transition is complete, complications will arise. For example, United States Patent Application Publication No. 2008/0031847 recites use of a phase transition composition during bowel resection. If the phase transition composition is not completely in the solid phase, cutting the bowel can result in septicemia.

In view of the above, there is an ongoing need to develop means to ensure in vivo delivery of a phase transition composition substantially in one phase or the other. It would be beneficial if such means could be used to control the temperature of any composition delivered from a syringe such that the attending clinician could immediately inject that composition into the patient.

It should be noted that all patents, patent applications, and literature references described herein are incorporated by reference in their entirety.

SUMMARY OF THE INVENTION

Described herein is a syringe having temperature modulation capabilities, particularly with regard to changing the temperature of the material being ejected from or injected into the syringe.

In one of its article of manufacture aspects, there is provided a temperature modulated syringe assembly (1) containing a phase transition composition which assembly (1) comprises:

a hollow syringe barrel (5) having a chamber (7) wherein said chamber (7) contains a phase transition composition which undergoes a transition from a liquid phase to a solid phase at or above a defined temperature or temperature range;

a distal end (9) of said barrel (5) having an aperture (11) there through;

a proximal end (13) of said barrel (5) having a passageway (15) there through communicating with said chamber (7);

means (17) for injecting/ejecting the composition from the barrel (5) through the aperture (11); and a heating or cooling element (21) optionally having operational control (23), which element (21) is contained over or within said aperture (11) and/or said distal end (9) of the barrel (5).

In one embodiment, the heating or cooling element (21) overlays said aperture (11) and/or said distal end (9) of the barrel (5).

In another embodiment, the heating or cooling element (21) is contained within said aperture (11) and/or said distal end (9) of the barrel (5), and the heating element (21) contains a further passageway (19) there though to permit injection/ejection of the phase transition composition out of the distal end (9) of said barrel (5).

In one embodiment, the heating or cooling element (21) is a heating element. In another embodiment, the heating or cooling element (21) is a cooling element. In an optional embodiment, the barrel (5) can be overlayed with either a cooling or heating element (21) with the opposite of a heating or cooling element (21). That is to say that if heating or cooling element (21) is a heating element, then barrel (5) can be overlayed with a cooling element (21) so that the phase transition composition remains in its cooler phase prior to ejection. Likewise, if heating or cooling element (21) is a cooling element, then barrel (5) can be overlayed with a heating element (21) so that the phase transition composition remains in its warmer phase prior to ejection.

In one embodiment, is provided a temperature modulated syringe assembly (1) containing a phase transition composition which assembly (1) comprises:

a hollow syringe barrel (5) having a chamber (7) wherein said chamber (7) contains a phase transition composition which undergoes a transition from a liquid phase to a solid phase at or above a defined temperature or temperature range;

a distal end (9) of said barrel (5) having an aperture (11) there through;

a proximal end (13) of said barrel (5) having a passageway (15) there through communicating with said chamber (7);

means (17) for injecting/ejecting the composition from the barrel (5) through the aperture (11);

a cannula or catheter (27) attached to the distal end (9) of the barrel; and a heating or cooling element (21) optionally having operational control (23), which element (21) is contained over or within said cannula or catheter.

In another embodiment is provided a temperature modulated syringe assembly (1) comprising:

a hollow syringe barrel (5) having a chamber (7) wherein said chamber (7) is adapted for containing a phase transition composition which undergoes a transition from a liquid phase to a solid phase at or above a defined temperature or temperature range;

a distal end (9) of said barrel (5) having an aperture (11) there through;

a proximal end (13) of said barrel (5) having a passageway (15) there through communicating with said chamber (7);

means (17) for injecting/ejecting the composition from the barrel (5) through the aperture (11);

optionally a cannula or catheter (27) attached to the distal end (9) of the barrel; and a heating or cooling element (21) optionally having operational control (23), which element (21) is contained over or within said aperture (11) and/or said distal end (9) of the barrel (5) or, alternatively, said element (21) is contained or within said cannula or catheter.

Another embodiment is directed to a kit of parts comprising:
1) a syringe as described herein; and
2) a vial or ampoule comprising a phase transition composition.

In a preferred embodiment, the phase transition composition comprises a poloxamer or a mixture of poloxamers. In such an embodiment, the phase transition composition is liquid below its phase transition temperature and solid or gel-like above its phase transition temperature.

In one of its method aspects, there is provided a method for delivering a phase transition composition in vivo in a second phase from a syringe wherein the composition is maintained in its first phase which method comprises loading the composition in its first phase into the temperature modulating syringe described above; activating the heating or cooling element of the syringe to a temperature such that the composition passing through that element is converted from its first phase to its second phase before existing the syringe; and then ejecting the composition in its second phase from the syringe.

DETAILED DESCRIPTION OF THE INVENTION

Definitions

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "distal end" refers to the end furthest from the person holding the syringe and closest to the destination to where the phase transition composition is delivered.

The term "proximal end" refers to the end closest to the person holding the syringe and furthest from the destination to where the phase transition composition is delivered.

The term "about" when used before a numerical designation, e.g., temperature, time, amount, and concentration, including range, indicates approximations which may vary by (+) or (−) 10%, 5% or 1%.

The term "heating element" is used relative to the temperature of the phase transition composition in the barrel of the syringe. For example, if the phase transition composition has a phase transition temperature at about 10° C.±5° C. and is stored in the barrel of the syringe at a temperature below 10° C., then the heating element is any element capable of warming the composition to above its phase transition temperature regardless of whether that temperature is below, at, or above room temperature. For example, it may be an electric heater made of metal or other suitable material and which may be capable of generating heat by an electric source, for example batteries.

The term "cooling element" is used relative to the temperature of the phase transition composition in the barrel of the syringe. For example, if the phase transition composition has phase transition temperature at about 15° C.±5° C. and is stored in a stock container at room temperature, then the cooling element is any element capable of cooling the composition to at or below its phase transition temperature regardless of whether that temperature is below, at, or above room temperature. For example, it may be an electric cooler made of metal or other suitable material which may be capable of cooling by electric source, for example batteries.

The term "subject," "individual" or "patient" is used interchangeably herein, and refers to a vertebrate, for example a mammal or a human. Mammals include, but are not limited to, murines, rats, simians, humans, farm animals, sport animals and pets.

Device

This invention is directed to a syringe having temperature modulation capabilities particularly with regard to changing the temperature of the material being ejected from or injected into the syringe.

In one of its article of manufacture aspects, there is provided a temperature modulated syringe assembly (1) containing a phase transition composition which assembly (1) comprises:

- a hollow syringe barrel (5) having a chamber (7) wherein said chamber (7) contains a phase transition composition which undergoes a transition from a liquid phase to a solid phase at or above a defined temperature or temperature range;
- a distal end (9) of said barrel (5) having an aperture (11) there through;
- a proximal end (13) of said barrel (5) having a passageway (15) there through communicating with said chamber (7);
- means (17) for injecting/ejecting the composition from the barrel (5) through the aperture (11); and
- a heating or cooling element (21) optionally having operational control (23), which element (21) is contained over or within said aperture (11) and/or said distal end (9) of the barrel (5).

In some embodiments, there is provided a temperature modulated syringe assembly (1) containing a phase transition composition which assembly (1) comprises:

- a hollow syringe barrel (5) having a chamber (7) wherein said chamber (7) contains a phase transition composition which undergoes a transition from a liquid phase to a solid phase at or above a defined temperature or temperature range and further wherein said composition is maintained in the barrel (5) in its liquid phase;
- a distal end (9) of said barrel (5) having an aperture (11) there through;
- a proximal end (13) of said barrel (5) having a passageway (15) there through communicating with said chamber (7);
- means (17) for injecting/ejecting the composition from the barrel (5) through the aperture (11);
- a heating or cooling element (21) optionally having operational control (23) which element (21) is contained over or within said aperture (11) and/or said distal end (9) of the barrel (5) wherein said heating or cooling element (21) when operated is capable of phase transitioning the composition from its liquid phase to its solid phase and further wherein, when said heating or cooling element (21) is contained within said aperture (11) and/or said distal end (9) of the barrel (5), said heating or cooling element (21) contains a passageway (19) there though to permit injection/ejection of the composition out of the distal end (9) of said barrel (5).

The capacity of the syringe, size of the aperture, and amount of heat may depend on the specific application the syringe assembly, so as to provide sufficient heat capacity to transition the desired phase transition composition to the desired temperature at the desired flow rate.

In some embodiments, the syringe has a size similar to a medical syringe. For example, the chamber (7) of the syringe may be able to contain from about 0.1 mL to about 10 mL of the phase transition composition.

In some embodiments, the aperture (11) has an outer diameter of about the diameter of a tubular tissue to which the phase transition composition is delivered, for example a blood vessel, vas deferen, fallopian tube, or intestinal tract. In some embodiments, the aperture (11) is further connected to a cannula (27) to facilitate delivery of the phase transition composition to the desired tissue.

The aperture (11) may be a tube made from a material with high thermal capacity, such as stainless steel, which is heated or cooled, actively or passively, by the heating or cooling element (21) so that the phase transition composition changes from a first phase to a second phase when it is pressed through the aperture (11) by the means (17) for injecting/ejecting. The aperture (11) may be permanently attached to the syringe barrel (5) or may be removable. For example, the aperture (11) may comprise a locking mechanism, such as male and/or female luer locks (26), on one or both ends of the aperture allowing it to fit directly onto the syringe barrel (5) and/or the cannula (27).

The barrel (5) of the syringe in operational form comprises means (17) for injecting/ejecting and a chamber (7) which prior to and during ejection holds the phase transition composition.

The means (17) for injecting/ejecting the composition from the barrel (5) may be a rigid plunger rod having, on the distal end, a stopper (17) slidably positioned in fluid-tight engagement inside the barrel (5)/chamber (7). The stopper is capable of moving fluid from chamber (7) through aperture (11) upon its movement toward the distal end (9) of the barrel (5). The stopper is also capable of facilitating the drawing of the phase transition composition into the chamber (7) through the aperture (11) upon its movement away from distal end (9). The proximal end (28) of the rigid plunger rod extends outwardly from the proximal end of the barrel (5), through aperture (15). Preferably, the proximal end (28) of the plunger rod flange is in a disc shape to provide a convenient structure for applying forces to move the plunger rod with respect to the syringe barrel (5). Alternatively, the syringe may be adapted such that the means for ejecting the composition may be a piston operated by gas, such as air.

Figure 1:
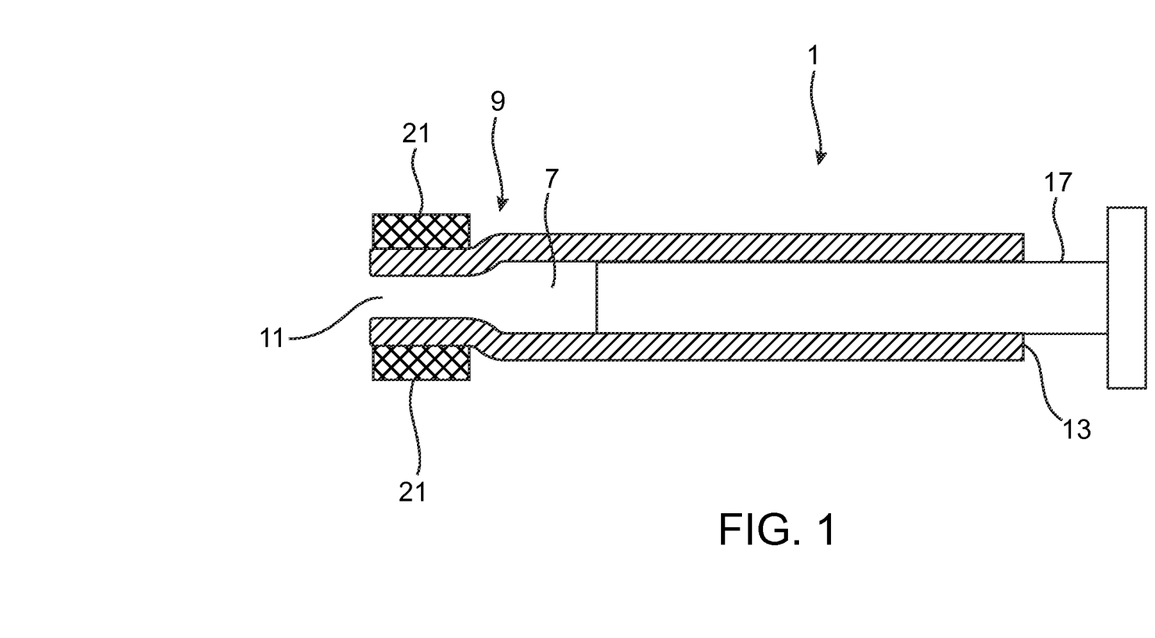
FIG. 1 illustrates an embodiment of a temperature modulating syringe of this invention wherein the heating or cooling element is contained over the aperture of the syringe.

In one embodiment, the heating or cooling element (21) overlays said aperture (11) and/or said distal end (9) of the barrel (5).

Figure 2:
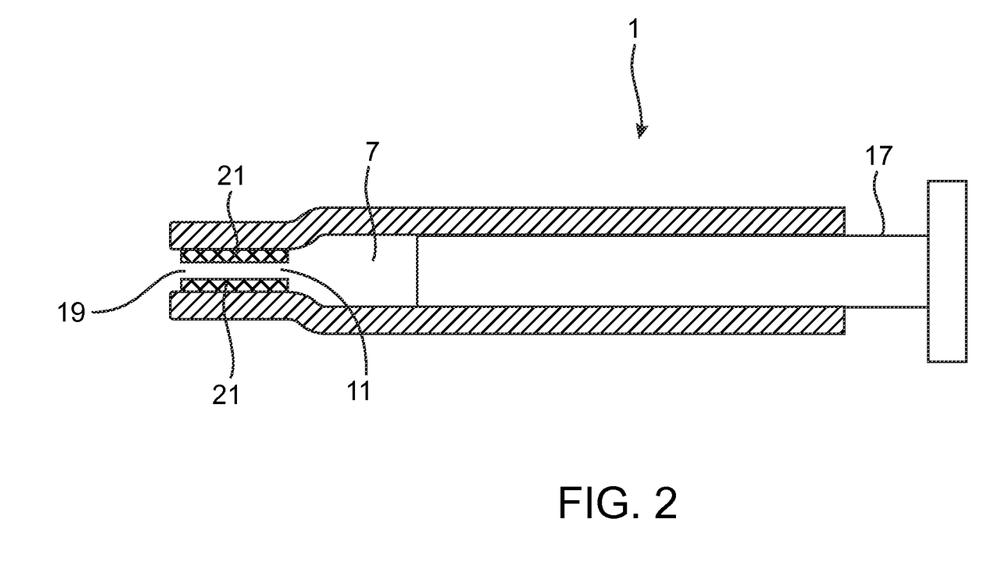
FIG. 2 illustrates an embodiment of a temperature modulating syringe of this invention wherein the heating or cooling element is located within the aperture of the syringe.

In another embodiment, the heating or cooling element (21) is contained within said aperture (11) and/or said distal end (9) of the barrel (5), said the heating or cooling element (21) contains a further passageway (19) there though to permit injection/ejection of the phase transition composition out of the distal end (9) of said barrel (5).

In one embodiment, the heating or cooling element (21) is a heating element. In another embodiment, the heating or cooling element (21) is a cooling element. In an optional embodiment, the barrel (5) can be overlayed with either a cooling or heating element (21) which is opposite that of heating or cooling element (21). That is to say that if heating or cooling element (21) is a heating element, then barrel (5) can be overlayed with a cooling element (21) so that the phase transition composition remains in its cooler phase prior to ejection. Likewise, if heating or cooling element (21) is a cooling element, then barrel (5) can be overlayed with a heating element (21) so that the phase transition composition remains in its warmer phase prior to ejection. The length of the heating or cooling element (21) may be the same as the aperture (11) or shorter or longer than the aperture (11). In one embodiment, the length of the heating or cooling element (21) is substantially the same length as the aperture (11). In a further embodiment, the housing of the device is made of an insulating material to further assist in maintaining the temperature of the device.

Figure 3:
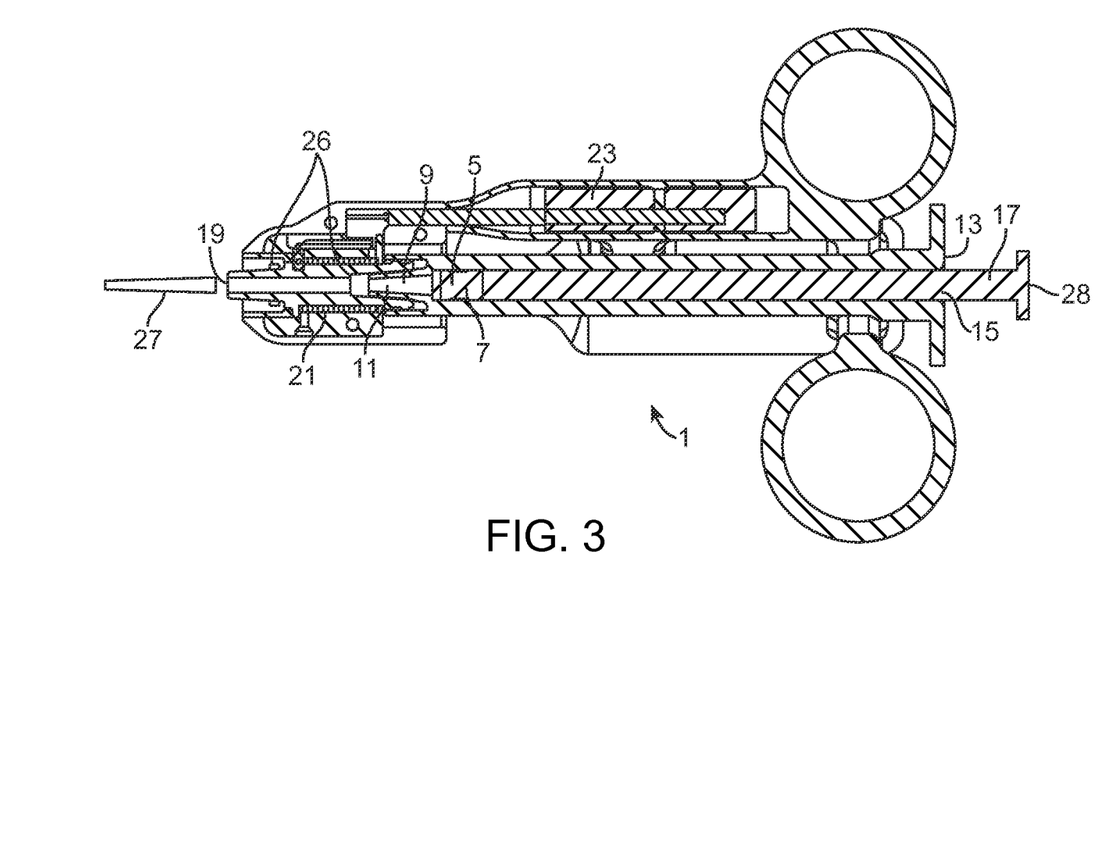
FIG. 3 illustrates an embodiment of a temperature modulating syringe of this invention.

In another embodiment, the syringe (1) is attached at its distal end to a cannula or catheter (27) *in* manners described above for attachment directly to the syringe. The cannula or catheter (27)*is* in fluid communication with the syringe barrel (5) and/or chamber (7). In this embodiment, the heating or cooling element (21) may be attached to or contained within the cannula or catheter. In one embodiment, the heating or cooling element (21) may be placed at the distal end of the catheter (27) or cannula.

Figure 4:
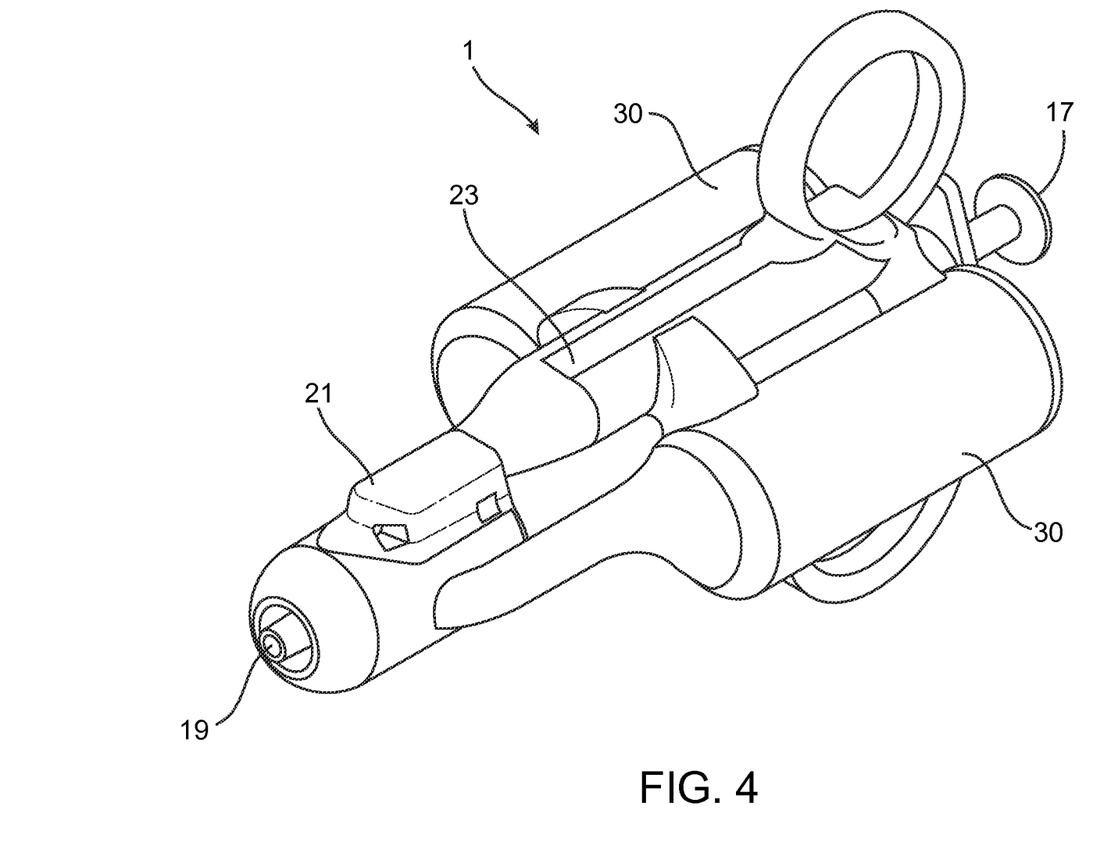
FIG. 4 illustrates the attachment of batteries to the temperature modulating syringe as a source of energy for the heating or cooling element of the syringe.

In another embodiment, the syringe assembly (1) further comprises an electricity source (30), such as a battery, for the heating or cooling element (21) to generate heat or cooling. In some embodiments, the heating or cooling element is activated by an on/off control which located either on the device or remotely.

In one embodiment, the phase transition composition comprises a poloxamer or a mixture of poloxamers. In such an embodiment, the phase transition composition is liquid below its phase transition temperature and solid or gel-like above the phase transition temperature.

The article of manufacture of this invention may be made of any suitable material known in the art, for example, plastic, glass, metal, etc. Each part of the article of manufacture may be made of the same or different material. In one embodiment, the material is able to be sterilized. In still another embodiment, the device is able to under go radiation sterilization or ethylene oxide sterilization.

Methods

In one of its method aspects, there is provided a method for delivering a phase transition composition in vivo in a second phase from a syringe wherein the composition is maintained in its first phase which method comprises loading the composition in its first phase into the temperature modulating syringe described above; activating the heating or cooling element of the syringe to a temperature such that composition passing through that element is converted from its first phase to its second phase before exiting the syringe and/or cannula or catheter, if present; and then ejecting the composition in its second phase from the syringe.

Compositions

The syringe assembly of this invention may be used to deliver any phase transition composition that require controlled phase transition from its first phase when being stored in the syringe barrel (5) to a second phase when passing through the aperture (11). Non-limiting examples of such phase transition compositions include those disclosed in U.S. Pat. No. 8,172,861, and U.S. Patent Publication 2010-0204718, which are incorporated herein by reference in their entirety. Additional phase transition compositions are described in U.S. Pat. Nos. 8,216,259 and 8,197,499 and U.S. Patent Publication No. 2008-0262519, which are also incorporated by reference in their entirety.

U.S. Pat. No. 8,172,861 discloses certain poloxamer compositions having a mixture of poloxamer 188 and poloxamer 407, specifically, poloxamer compositions having a) about 25 to 33% of a mixture of poloxamer 407 and poloxamer 188 in a ratio of between 3:1 and 0.8:1; and
b) an aqueous salt solution having an ionic strength of 0.05 M to 0.4 M.

U.S. Patent Publication No. 2010-0204718, which is incorporated by reference in its entirety, discloses poloxamer compositions with more than 35% w/w of total poloxamer concentration. Preferred embodiments of these compositions have a high elastic modulus of more than 20,000 Pascals, or more than 40,000 Pascals, or more than 50,000 Pascals, making them particularly useful in maintaining the shape of a filled lumen during an anastomosis procedure.

Thus, in one embodiment, the poloxamer composition comprises poloxamer 407 or poloxamer 188 or a mixture thereof, which composition has a transition temperature of from 0° C. to 40° C. and a gel phase elastic modulus of at least 20,000 Pascals at the operating temperature. In some embodiments, the gel phase elastic modulus is at least about 40,000 Pascals at the operating temperature. In some embodiments, the gel phase elastic modulus is at least about 50,000 Pascals at the operating temperature. Such phase transition compositions are preferably delivered to a tissue of a patient in a gel phase in certain applications. However, due to the high gel phase elastic modulus of certain phase transition compositions, if such compositions are in a gel phase in the syringe barrel before being ejected through the aperture, the composition would be too stiff and may require excessive force to be pushed through the narrow aperture, and may not be able to go through the aperture. The excessive force would affect the accuracy of the application of the phase transition composition or cause damages to the target tissue. Surprisingly, it was found that using the syringe of this invention with temperature modulation capabilities, it is possible to induce rapid phase transition of the phase transition composition when the phase transition composition is being ejected through the aperture, and still allow smooth ejection of the composition in a gel phase without the need to apply excessive force, which allows the physician doing the procedure better control of the delivery of the phase transition composition to the target tissue.

In one embodiment, the poloxamer composition comprises:

a) more than 35% w/w of poloxamer 407 or poloxamer 188 or a mixture thereof; and
b) an aqueous salt solution having an ionic strength of 0.05 M to 0.4 M.

In one embodiment, the poloxamer composition consists essentially of:

a) more than 35% w/w of poloxamer 407 or poloxamer 188 or a mixture thereof; and
b) an aqueous salt solution having an ionic strength of 0.05 M to 0.4 M.

In one embodiment, the poloxamer composition comprises up to about 48% w/w of poloxamer 188 or poloxamer 407 or a mixture thereof.

In one embodiment, the poloxamer composition comprises up to about 55% w/w of poloxamer 188 or poloxamer 407 or a mixture thereof.

In one aspect, the poloxamer composition comprises from about 15 to about 50% w/w poloxamer. In another aspect, the poloxamer composition comprises from about 35 to about 48% w/w poloxamer. In another aspect, the poloxamer composition comprises from about 49 to about 50% w/w poloxamer.

In some embodiments, the poloxamer composition comprises about 35.2 to about 48% w/w of poloxamer 188 or poloxamer 407 or a mixture thereof. In one aspect, the poloxamer composition comprises more than about 36% w/w, at least about 37% w/w, or at least about 39% w/w of poloxamer 188 or poloxamer 407 or a mixture thereof.

In one embodiment, the poloxamer composition comprises about 40% w/w of poloxamer 188 or a mixture of poloxamer 188 and poloxamer 407.

In one embodiment, the composition comprises about 36% w/w of a mixture of poloxamer 188 and poloxamer 407 in a ratio of at least about 1.3:1.

In one embodiment, the composition comprises about 36% w/w of a mixture of poloxamer 188 and poloxamer 407 in a ratio of about 1.5:1.

In one embodiment, the composition comprises up to about 48% w/w of poloxamer 188 or poloxamer 407 or a mixture thereof. In one particular embodiment, the composition comprises about 35.2 to about 48% w/w of poloxamer 188 or poloxamer 407 or a mixture thereof.

In one embodiment, the salt of the aqueous salt solution is selected from the group consisting of sodium chloride (NaCl), potassium chloride (KCl), sodium sulfate ($Na_2SO_4$), sodium bisulfate ($NaHSO_4$), sodium phosphate ($Na_3PO_4$), monosodium phosphate ($NaH_2PO_4$), disodium phosphate ($Na_2HPO_4$), potassium phosphate ($K_3PO_4$), monopotassium phosphate ($KH_2PO_4$), dipotassium phosphate ($K_2HPO_4$), various soluble calcium and magnesium salts, such as calcium chloride ($CaCl_2$), magnesium chloride ($MgCl_2$), and the like. Other salts include a combination of a cation selected from the group consisting of sodium, potassium, calcium, magnesium, ammonium, and tetraalkylammonium, with an anion selected from the group consisting of chloride, bromide, tartrate, mesylate, acetate, maleate, and oxalate and other biocompatible, water soluble salts including those described in P. Heinrich Stahl, Camille G. Wermuth (Eds.), Handbook of Pharmaceutical Salts Properties, Selection, and Use; 2002. A combination of any two or more salts can be used.

In one embodiment, the aqueous salt solution has an ionic strength that is equal to the ionic strength of a solution having a pH of about 7.4 and comprising a salt concentration of between 68 mM of sodium chloride, 1.3 mM of potassium chloride and 5 mM of phosphate ion to 274 mM of sodium chloride, 5.4 mM of potassium chloride, and 20 mM of phosphate ion.

In one embodiment, the aqueous salt solution is phosphate buffered saline.

In one embodiment, the pH of the composition is 5-9. In another embodiment, the pH of the composition is 6-8.

In one embodiment, the poloxamer composition comprises:
about 14.4% w/w of poloxamer 407;
about 21.6% w/w of poloxamer 188;
and about 64% w/w of phosphate buffered saline solution.

In one embodiment, the poloxamer composition comprises:
about 45% w/w of poloxamer 188;
and about 55% w/w of phosphate buffered saline solution.

In one embodiment, the poloxamer composition comprises:
about 49.1% w/w of poloxamer 188;
and about 50.9% w/w of phosphate buffered saline solution.

Kit of Parts

In one embodiment, a kit of parts is contemplated. The kit contains a syringe as described above and a container, vial or ampoule of the phase transition composition. In one embodiment, the syringe comprises:

a hollow syringe barrel (5) having a chamber (7) wherein said chamber (7) is adapted for containing a phase transition composition which undergoes a transition from a liquid phase to a solid phase at or above a defined temperature or temperature range;

a distal end (9) of said barrel (5) having an aperture (11) there through;

a proximal end (13) of said barrel (5) having a passageway (15) there through communicating with said chamber (7);

means (17) for injecting/ejecting the composition from the barrel (5) through the aperture (11);

optionally a cannula or catheter (27) attached to the distal end (9) of the barrel; and a heating or cooling element (21) optionally having operational control (23), which element (21) is contained over or within said aperture (11) and/or said distal end (9) of the barrel (5) or, alternatively, said element (21) is contained or within said cannula or catheter.

As mentioned above, the kit of parts also comprises the phase transition composition. The composition is as described throughout.

In one embodiment, the phase transition composition is sterilized. In one embodiment the syringe is sterilized. It is contemplated that the composition and syringe may be sterilized by the same or different methods, including by not limited to, autoclave, e-beam, and the like. Further, it is contemplated that the syringe and composition may be packaged together or separately.

The preceding merely illustrates the principles and certain embodiments of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A temperature modulated syringe assembly (1) containing a phase transition composition which assembly (1) comprises:

a hollow syringe barrel (5) having a chamber (7) wherein said chamber (7) contains the phase transition composition which undergoes a transition from a liquid phase to a solid phase at or above a defined temperature or temperature range and further wherein said composition is maintained in the barrel (5) in its liquid phase;

a distal end (9) of said barrel (5) having an aperture (11) there through;

a proximal end (13) of said barrel (5) having a passageway (15) there through communicating with said chamber (7);

means (17) for injecting/ejecting the composition from the chamber (7) through the aperture (11);

a heating or cooling element (21) optionally having an operational control (23) which element (21) is contained within said aperture (11) and is not contained over and is not contained within said chamber (7), wherein said heating or cooling element (21) when operated is capable of phase transitioning the composition from its liquid phase to its solid phase and further wherein said heating or cooling element (21) contains a passageway (19) there through to permit injection/ejection of the composition out of the distal end (9) of said barrel (5).

2. A method for delivering a phase transition composition in a second phase from a syringe, wherein:

the syringe comprises:
- a hollow syringe barrel (5) having a chamber (7) wherein said chamber (7) contains the phase transition composition which undergoes a transition from a first phase to a second phase at or above a defined temperature or temperature range;
- a distal end (9) of said barrel (5) having an aperture (11) there through;
- a proximal end (13) of said barrel (5) having a passageway (15) there through communicating with said chamber (7);
- means (17) for injecting/ejecting the composition from the barrel (5) through the aperture (11); and
- a heating or cooling element (21) optionally having an operational control (23), which element (21) is contained over or within said aperture (11), and the composition is maintained in the first phase in the chamber (7) until the composition passes through the heating or cooling element (21), which method comprises activating the heating or cooling element to a temperature such that the composition is converted from the first phase to the second phase when passing through the element (21) and before exiting the syringe; and ejecting the composition in the second phase from the syringe.

3. The method of claim 2, wherein the phase transition composition comprises a poloxamer or a mixture of poloxamers.

4. A kit of parts comprising:
1) the syringe of claim 1; and
2) a vial or ampoule comprising a phase transition composition.

5. The kit of claim 4, wherein the phase transition composition comprises a poloxamer or a mixture of poloxamers.

6. A temperature modulated syringe assembly (1) containing a phase transition composition which assembly (1) comprises:
- a hollow syringe barrel (5) having a chamber (7) wherein said chamber (7) contains the phase transition composition which undergoes a transition from a liquid phase to a solid phase at or above a defined temperature or temperature range;
- a distal end (9) of said barrel (5) having an aperture (11) there through;
- a proximal end (13) of said barrel (5) having a passageway (15) there through communicating with said chamber (7);
- means (17) for injecting/ejecting the composition from the barrel (5) through the aperture (11); and
- a heating or cooling element (21) optionally having an operational control (23), which element (21) is contained over or within said aperture (11) such that the phase transition composition is contained in a first phase in the chamber (7) until the phase transition composition passes through the heating or cooling element (21) to be converted to a second phase, when the heating or cooling element is activated.

* * * * *